(12) United States Patent
Chatterton et al.

(10) Patent No.: US 8,940,887 B2
(45) Date of Patent: Jan. 27, 2015

(54) RNAI-MEDIATED INHIBITION OF HIF1A FOR TREATMENT OF OCULAR ANGIOGENESIS

(71) Applicant: Alcon Research, Ltd., Fort Worth, TX (US)

(72) Inventors: Jon E. Chatterton, Fort Worth, TX (US); David P. Bingaman, Weatherford, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/904,431

(22) Filed: May 29, 2013

(65) Prior Publication Data

US 2013/0245098 A1 Sep. 19, 2013

Related U.S. Application Data

(62) Division of application No. 13/474,405, filed on May 17, 2012, now Pat. No. 8,471,000, which is a division of application No. 13/113,782, filed on May 23, 2011, now abandoned, which is a division of application No. 12/706,014, filed on Feb. 16, 2010, now Pat. No. 7,981,870, which is a division of application No. 11/642,016, filed on Dec. 19, 2006, now abandoned.

(60) Provisional application No. 60/754,956, filed on Dec. 29, 2005.

(51) Int. Cl.
*C07H 21/04* (2006.01)
*A61K 48/00* (2006.01)
*C07H 21/02* (2006.01)

(52) U.S. Cl.
USPC .......................... 536/24.5; 514/44; 536/23.1

(58) Field of Classification Search
None
See application file for complete search history.

(56) References Cited

U.S. PATENT DOCUMENTS

| 7,217,572 | B2 | 5/2007 | Ward et al. |
| 2004/0101858 | A1 | 5/2004 | Ward et al. |
| 2004/0220393 | A1 | 11/2004 | Ward et al. |
| 2005/0255487 | A1 | 11/2005 | Khvorova et al. |

FOREIGN PATENT DOCUMENTS

| WO | 03085110 | A2 | 10/2003 | |
| WO | 2004042024 | A2 | 5/2004 | |
| WO | WO 2004/065583 | A2 * | 8/2004 | ............ 435/6 |
| WO | 2005032486 | A2 | 4/2005 | |
| WO | 2005035759 | A2 | 4/2005 | |
| WO | 2005116204 | A1 | 8/2005 | |
| WO | 2007002718 | A2 | 1/2007 | |

OTHER PUBLICATIONS

Canadian patent application No. 2,566,286 Abstract only; Corresponds to WO2005116204 dated Aug. 12, 2005; RNAi Co., Ltd.
Beppu, K., et al.; "Topotecan blocks hypoxia-inducible factor-1alpha and vascular endothelial growth factor expression induced by insulin-like growth factor-I in neuroblastoma cells"; Cancer Res.; 65:47775-4781; 2005.
Freeman, R.S., et al.; "Targeting hypoxia-inducible factor (HIF) as a therapeutic strategy for CNS disorders"; Curr Drug Targets CNS Neurol Disord. 4:85-92; 2005.
Kim, B., et al.; "Inhibition of ocular angiogenesis by siRNA targeting vascular endothelial growth factor pathway genes: therapeutic strategy for herpetic stromal keratitis"; Am J Pathol. 165:2177-2185; 2004.
Kim, D.H., et al.; "Synthetic dsRNA dicer substrates enhance RNAi potency and efficacy"; Nature Biotechnology; 23:2;222-226.
Li, L. et al.; "Evaluating hypoxia-inducible factor-1alpha as a cancer therapeutic target via inducible RNA interference in vivo"; Cancer Res.; 65:7249-7258; 2005.
Mahato, et al.; "Modulation of gene expression by antisense and antigene oligodeoxynucleotides and small interfering RNA"; Expert Opin. Drug Deily.; vol. 2; No. 1; pp. 3-28; 2005.
Reich, S.J., et al.; "Small interfering Rna (siRNA) targeting VEGF effectively inhibits ocular neovascularization in a mouse model"; Mol Vis.; 9:210-216; 2003.
Ricker, J.L., et al.; "2-methoxyestradiol inhibits hypoxia-inducible factor 1alpha, tumor growth, and angiogenesis and augments paclitaxel efficacy in head and neck squamous cell carcinoma"; Clin Cancer Res. 10:8665-8673; 2004.
Scherer and Rossi; "Approaches for the sequence-specific knockdown of mRNA"; Nature Biotechnology; vol. 21; No. 12; pp. 1457-1465; Dec. 2003.
Shen, J. et al.; "Suppression of ocular neovascularization with siRNA targeting VEGF receptor 1"; Gene Ther.; 13:225-234; 2006.
Tolentino, M.J., et al; "Intravitreal injection of vascular endothelial growth factor small interfering RNA inhibits growth and leakage in a nonhuman primate, laser-induced model of choroidal neovascularization"; Retina; 24:132-138; 2004.
Wang, et al.; "Inhibition of Retinal Neovascularization by Intravitreous Delivery of HIF1a.siRNA in a Mice Model of Oxygen Induced Retinopathy"; IVOS; vol. 46, No. Suppl. S, 2005, p. 5202.
Zhang, X., et al.; "Enhancement of hypoxia-induced tumor cell death in vitro and radiation therapy in vivo by use of small interfering RNA targeted to hypoxia-inducible factor-1alpha"; Cancer Res. 64:8139-8142; 2004.
Zhang and Hua; "Targeted gene silencing by small interfering RNA-based knock-down technology"; Current Pharmaceutical Biotechnology; vol. 5; pp. 1-7; 2004.
Search report and IPER for corresponding PCT application No. US2006062293 dated Mar. 6, 2008.

* cited by examiner

*Primary Examiner* — Amy Bowman

(57) ABSTRACT

RNA interference is provided for inhibition of HIF1A mRNA expression for treating patients with ocular angiogenesis, particularly for treating retinal edema, diabetic retinopathy, sequela associated with retinal ischemia, posterior segment neovascularization (PSNV), and neovascular glaucoma, and for treating patients at risk of developing such conditions.

2 Claims, 1 Drawing Sheet

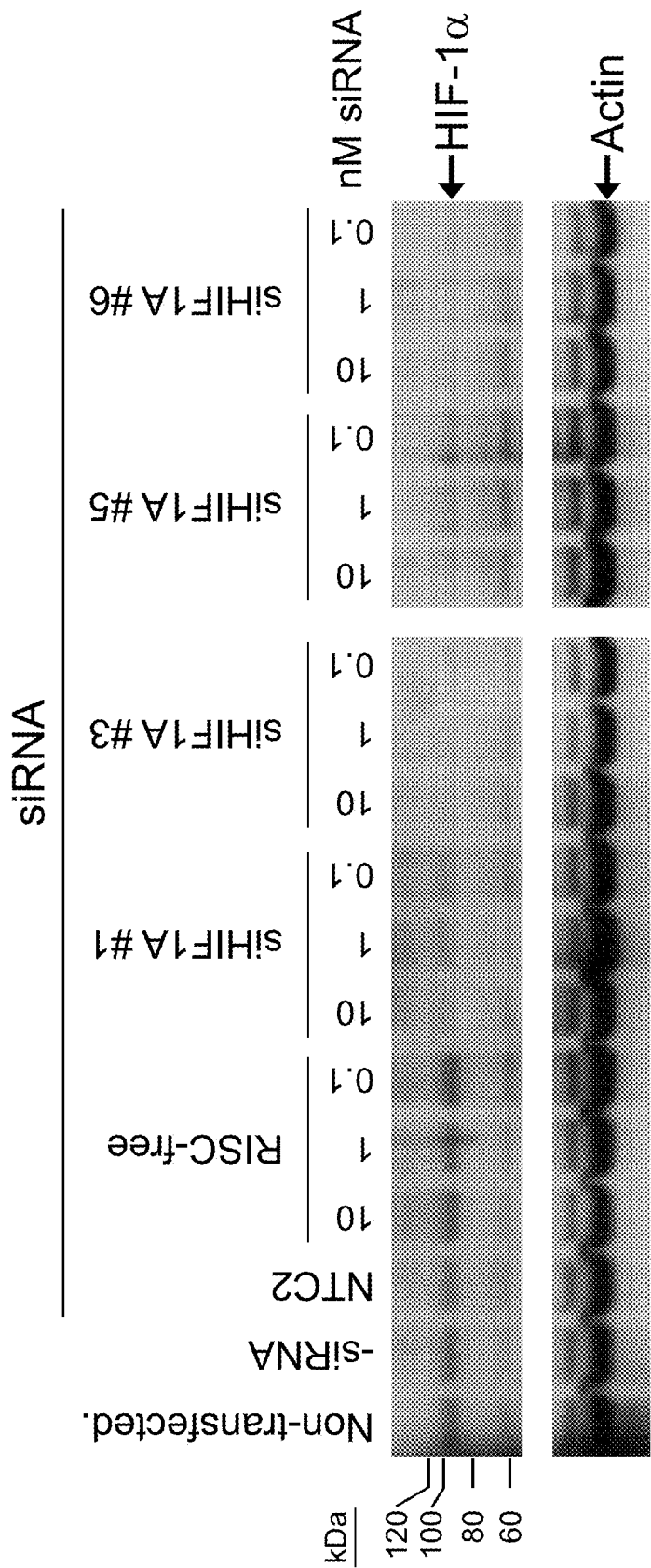

RNAI-MEDIATED INHIBITION OF HIF1A FOR TREATMENT OF OCULAR ANGIOGENESIS

The present application is a divisional of U.S. patent application Ser. No. 13/474,405 filed May 17, 2012, (now allowed), which is a divisional of U.S. patent application Ser. No. 13/113,782 filed May 23, 2011 (now abandoned), which is a divisional of U.S. patent Ser. No. 12/706,014 filed Feb. 16, 2010 (now U.S. Pat. No. 7,981,870), which claims benefit to U.S. patent application Ser. No. 11/642,016 filed Dec. 19, 2006 (now abandoned), which claims benefit to U.S. Provisional Patent Application Ser. No. 60/754,956 filed on Dec. 29, 2005, the disclosure of which is specifically incorporated by reference herein.

FIELD OF THE INVENTION

The present invention relates to the field of interfering RNA compositions for inhibition of expression of hypoxia-inducible factor-1α (HIF-1α), the protein encoded by HIF1A mRNA, in ocular angiogenesis, including those cellular changes resulting from the transcription factor activity of HIF-1α that lead directly or indirectly to ocular neovasularization, retinal edema, diabetic retinopathy, sequela associated with retinal ischemia, posterior segment neovascularization, and neovascular glaucoma, for example.

BACKGROUND OF THE INVENTION

Diabetic retinopathy (DR) is an eye disease that develops in diabetes due to changes in the cells that line blood vessels, i.e. the retinal microvascular endothelium. During diabetes mellitus, hyperglycemia can cause damage in a number of ways. For example, glucose, or a metabolite of glucose, binds to the amino groups of proteins, leading to tissue damage. In addition, excess glucose enters the polyol pathway resulting in accumulations of sorbitol. Sorbitol cannot be metabolized by the cells of the retina and can contribute to high intracellular osmotic pressure, intracellular edema, impaired diffusion, tissue hypoxia, capillary cell damage, and capillary weakening. Diabetic retinopathy involves thickening of capillary basement membranes which may in turn prevent pericytes, the predominant perivascular cell type in retinal capillaries, from contacting endothelial cells. Pericyte and endothelial cell death occurs through an apoptotic mechanism during diabetic retinopathy, where the loss of pericytes likely increases the permeability of the capillaries and leads to breakdown of the blood-retina barrier and blood flow dysregulation. Weakened capillaries lead to aneurysm formation and further leakage. These effects of hyperglycemia can also impair neuronal functions in the retina. DR is associated with retinal microaneurysms, hemorrhages, exudates, and retinitis proliferans, i.e., massive neovascular and connective tissue growth on the inner surface of the retina. Diabetic retinopathy may be of the background type, progressively characterized by microaneurysms; intraretinal punctate hemorrhages; yellow, waxy exudates; cotton-wool patches; and macular edema. This is an early stage of diabetic retinopathy termed nonproliferative diabetic retinopathy.

As the diabetes-induced microvascular pathology progress, retinal capillaries eventually become occluded and lead to multifocal areas of ischemia hypoxia within the retina. Hypoxic conditions in the non-perfused tissue causes an increase in HIF-1α levels. The resulting changes in HIF-1-mediated gene expression elicits the production of growth factors capable of stimulating abnormal new blood vessel growth from existing vessels (angiogenesis). These pathologic new blood vessels grow into the vitreous and can cause loss of sight, a condition called proliferative diabetic retinopathy (PDR), since the new blood vessels are fragile and tend to leak blood into the eye. The proliferative type of DR is characterized by neovascularization of the retina and optic disk which may project into the vitreous, proliferation of fibrous tissue, vitreous hemorrhage, and retinal detachment.

Neovascularization also occurs in a type of glaucoma called neovascular glaucoma in which increased intraocular pressure is caused by growth of connective tissue and new blood vessels upon the trabecular meshwork. Neovascular glaucoma is a form of secondary glaucoma caused by neovascularization in the chamber angle.

Posterior segment neovascularization (PSNV) is a vision-threatening pathology responsible for the two most common causes of acquired blindness in developed countries: exudative age-related macular degeneration (AMD) and PDR. Until recently, the only approved treatments for PSNV that occurs during exudative AMD were laser photocoagulation or photodynamic therapy with VISUDYNE™. Both therapies involve occlusion of affected vasculature, which results in permanent, laser-induced damage to the retina, and does not address the underlying cause of neovascularization. Recurrence of neovascularization from the same area is common. For patients with PDR, surgical interventions with vitrectomy and removal of preretinal membranes are the only options currently available, as well as a laser therapy called panretinal photocoagulation to prevent the production of more new vessels.

Current pharmaceutical efforts have focused on inhibiting the effects of potent angiogenic factors such as VEGF, a gene that is regulated by HIF-1. Recently, intravitreal injection of LUCENTIS™, an anti-VEGF antibody fragment, was approved for treatment of AMD. This antibody fragment was designed to bind to and inhibit VEGF to inhibit the formation of new blood vessels. Lucentis is also in clinical trials for the treatment of diabetic macular edema. Other approaches include the use of small interfering RNA targeting VEGF or its receptor.

Disruption of the interaction between the HIF-1 transcription factor and the hypoxia response element in oxygen sensitive promoters using conventional small molecule inhibitors is likely to be very difficult. Like VEGF, HIF1A is not considered to be "druggable" in the classical sense. Furthermore, the silencing of individual downstream effectors of HIF-1, such as VEGF or RTP801, may only partially block neovascularization.

The present invention addresses the above-cited problems and provides interfering RNAs targeting HIF1A, the transcriptional control gene for downstream genes involved in angiogenesis and vascular permeability (edema).

SUMMARY OF THE INVENTION

The present invention is directed to interfering RNAs that silence HIF1A mRNA expression, thus decreasing transcriptional activity of HIF-1 inducible genes and treating ocular angiogenesis by effecting a lowering of ocular pre-angiogenic and angiogenic cellular activity.

The term "ocular angiogenesis," as used herein, includes ocular pre-angiogenic conditions and ocular angiogenic conditions, and includes those cellular changes resulting from the expression of HIF1-inducible genes that lead directly or indirectly to ocular angiogenesis, ocular neovasularization, retinal edema, diabetic retinopathy, sequela associated with retinal ischemia, PSNV, and neovascular glaucoma, for example.

The interfering RNAs of the invention are useful for treating patients with ocular angiogenesis, ocular neovasularization, retinal edema, diabetic retinopathy, sequela associated with retinal ischemia, posterior segment neovascularization (PSNV), and neovascular glaucoma, or patients at risk of developing such conditions, for example.

An embodiment of the present invention provides a method of attenuating expression of an HIF1A target mRNA in a subject. The method comprises administering to the subject a composition comprising an effective amount of interfering RNA having a length of 19 to 49 nucleotides and a pharmaceutically acceptable carrier. In one embodiment, administration is to an eye of the subject for attenuating expression of an ocular angiogenesis target in a human.

In one embodiment of the invention, the interfering RNA comprises a sense nucleotide strand, an antisense nucleotide strand and a region of at least near-perfect contiguous complementarity of at least 19 nucleotides. Further, the antisense strand hybridizes under physiological conditions to a portion of an mRNA corresponding to SEQ ID NO:1 or SEQ ID NO:2 which are the sense cDNA sequences encoding HIF1A variant 1 and variant 2, respectively (GenBank accession no. NM_001530 and NM_181054, respectively). The antisense strand has a region of at least near-perfect contiguous complementarity of at least 19 nucleotides with the hybridizing portion of mRNA corresponding to SEQ ID NO:1 or SEQ ID NO:2, respectively. The administration of such a composition attenuates the expression of an HIF1A target of the subject.

In one embodiment of the invention, an interfering RNA is designed to target an mRNA corresponding to SEQ ID NO:1 comprising nucleotide 411, 580, 583, 868, 869, 1099, 1100, 1242, 1302, 1371, 1396, 1559, 1560, 1809, 2085, 2087, 2105, 2138, 2256, 2358, 2422, 2636, 2666, 2743, 2858, 2861, 3135, 3544, 3554, 1943, 1791, 2351, or 1408.

In another embodiment of the invention, an interfering RNA is designed to target an mRNA corresponding to SEQ ID NO:2 comprising nucleotide 2360, 2411, 2420, 2536, 2539, 2545, 2616, 2731, 2734, 3008, or 3427.

The present invention further provides for administering a second interfering RNA to a subject in addition to a first interfering RNA. The method comprises administering to the subject a second interfering RNA having a length of 19 to 49 nucleotides and comprising a sense nucleotide strand, an antisense nucleotide strand, and a region of at least near-perfect contiguous complementarity of at least 19 nucleotides; wherein the antisense strand of the second interfering RNA hybridizes under physiological conditions to a second portion of mRNA corresponding to SEQ ID NO:1 or SEQ ID NO:2 and the antisense strand has a region of at least near-perfect contiguous complementarity of at least 19 nucleotides with the second hybridizing portion of mRNA corresponding to SEQ ID NO:1 or SEQ ID NO:2, respectively. Further, a third, fourth, or fifth, etc. interfering RNA may be administered in a similar manner.

Another embodiment of the invention is a method of attenuating expression of HIF1A in a subject comprising administering to the subject a composition comprising an effective amount of single-stranded interfering RNA having a length of 19 to 49 nucleotides and a pharmaceutically acceptable carrier.

For attenuating expression of HIF1A, the single-stranded interfering RNA hybridizes under physiological conditions to a portion of mRNA corresponding to SEQ ID NO:1 comprising nucleotide 411, 580, 583, 868, 869, 1099, 1100, 1242, 1302, 1371, 1396, 1559, 1560, 1809, 2085, 2087, 2105, 2138, 2256, 2358, 2422, 2636, 2666, 2743, 2858, 2861, 3135, 3544, 3554, 1943, 1791, 2351, or 1408, and the interfering RNA has a region of at least near-perfect contiguous complementarity of at least 19 nucleotides with the hybridizing portion of mRNA corresponding to SEQ ID NO: 1. In another embodiment, for attenuating expression of HIF1A, the single-stranded interfering RNA hybridizes under physiological conditions to a portion of mRNA corresponding to SEQ ID NO:2 comprising nucleotide 2360, 2411, 2420, 2536, 2539, 2545, 2616, 2731, 2734, 3008, or 3427. Expression of HIF1A is thereby attenuated.

A further embodiment of the invention is a method of treating ocular angiogenesis in a subject in need thereof. The method comprises administering to an eye of the subject a composition comprising an effective amount of interfering RNA having a length of 19 to 49 nucleotides and a pharmaceutically acceptable carrier, the interfering RNA comprising a sense nucleotide strand, an antisense nucleotide strand, and a region of at least near-perfect contiguous complementarity of at least 19 nucleotides. The antisense strand hybridizes under physiological conditions to a portion of mRNA corresponding to SEQ ID NO:1 or SEQ ID NO:2 and has a region of at least near-perfect contiguous complementarity of at least 19 nucleotides with the hybridizing portion of mRNA corresponding to SEQ ID NO:1 or SEQ ID NO:2, respectively. The ocular angiogenesis is treated thereby.

Another embodiment of the invention is a method of treating ocular angiogenesis in a subject in need thereof, the method comprising administering to an eye of the subject a composition comprising an effective amount of interfering RNA having a length of 19 to 49 nucleotides and a pharmaceutically acceptable carrier, the interfering RNA comprising a region of at least 13 contiguous nucleotides having at least 90% sequence complementarity to, or at least 90% sequence identity with, the penultimate 13 nucleotides of the 3' end of an mRNA corresponding to any one of SEQ ID NO:3 and SEQ ID NO:9-SEQ ID NO:51, wherein the ocular angiogenesis is treated thereby.

Another embodiment of the invention is a method of attenuating expression of an HIF1A target mRNA in a subject, comprising administering to the subject a composition comprising an effective amount of interfering RNA having a length of 19 to 49 nucleotides and a pharmaceutically acceptable carrier, where the interfering RNA comprises a region of at least 13 contiguous nucleotides having at least 90% sequence complementarity to, or at least 90% sequence identity with, the penultimate 13 nucleotides of the 3' end of an mRNA corresponding to any one of SEQ ID NO:3 and SEQ ID NO:9-SEQ ID NO:51.

In a further embodiment of the present invention, the region of contiguous nucleotides is a region of at least 14 contiguous nucleotides having at least 85% sequence complementarity to, or at least 85% sequence identity with, the penultimate 14 nucleotides of the 3' end of an mRNA corresponding to the sequence of the sequence identifier. In yet another embodiment of the invention, the region of contiguous nucleotides is a region of at least 15, 16, 17, or 18 contiguous nucleotides having at least 80% sequence complementarity to, or at least 80% sequence identity with, the penultimate 15, 16, 17, or 18 nucleotides, respectively, of the 3' end of an mRNA corresponding to the sequence identified by the sequence identifier.

A further embodiment of the invention is a method of treating ocular angiogenesis in a subject in need thereof, the method comprising administering to the subject a composition comprising a double stranded siRNA molecule that down regulates expression of a HIF1A gene via RNA interference, wherein each strand of the siRNA molecule is independently about 19 to about 27 nucleotides in length; and one strand of the siRNA molecule comprises a nucleotide sequence having substantial complementarity to an mRNA corresponding to the HIF1A gene, respectively, so that the siRNA molecule directs cleavage of the mRNA via RNA interference.

A composition comprising interfering RNA having a length of 19 to 49 nucleotides and having a nucleotide sequence of any one of SEQ ID NO:3, and SEQ ID NO:9-SEQ ID NO:51, or a complement thereof, and a pharmaceutically acceptable carrier is an embodiment of the present invention. In one embodiment, the interfering RNA is isolated. The term "isolated" means that the interfering RNA is free of its total natural mileau.

Another embodiment of the invention is a composition comprising a double stranded siRNA molecule that down regulates expression of a HIF1A gene via RNA interference, wherein each strand of the siRNA molecule is independently about 19 to about 27 nucleotides in length; and one strand of the siRNA molecule comprises a nucleotide sequence has substantial complementarity to an mRNA corresponding to the HIF1A gene, respectively, so that the siRNA molecule directs cleavage of the mRNA via RNA interference.

Use of any of the embodiments as described herein in the preparation of a medicament for attenuating expression of HIF1A mRNA is also an embodiment of the present invention.

BRIEF DESCRIPTION OF THE DRAWING

The FIGURE provides a HIF-1α western blot of HeLa cells transfected with HIF1A siRNAs #1, #3, #5, and #6, and a RISC-free control siRNA, each at 10 nM, 1 nM, and 0.1 nM; a non-targeting control siRNA (NTC2) at 10 nM; and a buffer control (−siRNA). The arrows indicate the positions of the 93-kDa HIF-1α protein and the 42-kDa actin protein bands.

DETAILED DESCRIPTION OF THE INVENTION

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the antisense strand) can favor incorporation of the antisense strand into RISC.

RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA. Other RNA molecules and RNA-like molecules can also interact with RISC and silence gene expression. Examples of other RNA molecules that can interact with RISC include short hairpin RNAs (shRNAs), single-stranded siRNAs, microRNAs (miRNAs), and dicer-substrate 27-mer duplexes. The term "siRNA" as used herein refers to a double-stranded interfering RNA unless otherwise noted. Examples of RNA-like molecules that can interact with RISC include RNA molecules containing one or more chemically modified nucleotides, one or more deoxyribonucleotides, and/or one or more non-phosphodiester linkages. For purposes of the present discussion, all RNA or RNA-like molecules that can interact with RISC and participate in RISC-mediated changes in gene expression will be referred to as "interfering RNAs." SiRNAs, shRNAs, miRNAs, and dicer-substrate 27-mer duplexes are, therefore, subsets of "interfering RNAs."

Interfering RNA of embodiments of the invention appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

The present invention relates to the use of interfering RNA to inhibit the expression of hypoxia-inducible factor 1A (HIF1A), thus interfering with transcription of a number of genes that would otherwise be induced in response to reduced oxygen tension. According to the present invention, interfering RNAs as set forth herein, provided exogenously or expressed endogenously, are particularly effective at silencing of HIF1A mRNA.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

An mRNA sequence is readily deduced from the sequence of the corresponding DNA sequence. For example, SEQ ID NO:1 provides the sense strand sequence of DNA corresponding to the mRNA for HIF1A variant 1. The mRNA sequence is identical to the DNA sense strand sequence with the "T" bases replaced with "U" bases. Therefore, the mRNA sequence of HIF1A variant 1 is known from SEQ ID NO:1 and the mRNA sequence of HIF1A variant 2 is known from SEQ ID NO:2.

Hypoxia-Inducible Factor-1 mRNA (HIF1A Variant 1 and Variant 2):

Hypoxia-inducible factor (HIF-1) is a transcription factor that is responsible for changes in expression in a number of genes in response to reduced oxygen tension. HIF-1 is a heterodimer composed of alpha and beta subunits encoded by HIF1A and ARNT, respectively. At least two HIF-1-inducible genes have been implicated in pathological neovascularization in the retina including VEGF and RTP801 (REDD1).

Therefore, inhibition of expression of HIF1A is provided herein to attenuate transcription of such genes and activity of the gene products.

The GenBank database of the National Center for Biotechnology Information at ncbi.nlm.nih.gov provides the DNA sequence for HIF1A variant 1 as accession no. NM_001530, provided in the "Sequence Listing" as SEQ ID NO:1. SEQ ID NO:1 provides the sense strand sequence of DNA that corresponds to the mRNA encoding HIF1A variant 1 (with the exception of "T" bases for "U" bases). The coding sequence for HIF1A variant 1 is from nucleotides 285-2765.

Equivalents of the above-cited HIF1A variant 1 mRNA sequence are alternative splice forms, allelic forms, isozymes, or a cognate thereof. A cognate is an HIF1A mRNA from another mammalian species that is homologous to SEQ ID NO:1 (an ortholog).

The GenBank database of the National Center for Biotechnology Information at ncbi.nlm.nih.gov provides the DNA sequence for HIF1A variant 2 as accession no. NM_181054, provided in the "Sequence Listing" as SEQ ID NO:2. SEQ ID NO:2 provides the sense strand sequence of DNA that corresponds to the mRNA encoding HIF1A variant 2 (with the exception of "T" bases for "U" bases). The coding sequence for HIF1A variant 2 is from nucleotides 285-2492.

Equivalents of the above-cited HIF1A variant 2 mRNA sequence are alternative splice forms, allelic forms, isozymes, or a cognate thereof A cognate is an HIF1A variant 2 mRNA from another mammalian species that is homologous to SEQ ID NO:2 (an ortholog).

Attenuating Expression of an mRNA:

The phrase, "attenuating expression of an mRNA," as used herein, means administering or expressing an amount of interfering RNA (e.g., an siRNA) to reduce translation of the target mRNA into protein, either through mRNA cleavage or through direct inhibition of translation. The reduction in expression of the target mRNA or the corresponding protein is commonly referred to as "knock-down" and is reported relative to levels present following administration or expression of a non-targeting control RNA (e.g., a non-targeting control siRNA). Knock-down of expression of an amount including and between 50% and 100% is contemplated by embodiments herein. However, it is not necessary that such knock-down levels be achieved for purposes of the present invention. In one embodiment, a single interfering RNA targeting the HIF1A mRNA is administered to decrease production of HIF1A. In other embodiments, two or more interfering RNAs targeting the HIF1A target are administered to decrease expression. In still other embodiments, a first interfering RNA targeting the HIF1A variant 1 target and a second interfering RNA targeting the HIF1A variant 2 target are administered to decrease HIF1A expression.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

Inhibition of targets cited herein is also inferred in a human or mammal by observing an improvement in an ocular angiogenesis symptom such as improvement in retinal edema, diabetic retinopathy, retinal ischemia, or in posterior segment neovascularization (PSNV), for example.

Interfering RNA:

In one embodiment of the invention, interfering RNA (e.g., siRNA) has a sense strand and an antisense strand, and the sense and antisense strands comprise a region of at least near-perfect contiguous complementarity of at least 19 nucleotides. In a further embodiment of the invention, interfering RNA (e.g., siRNA) has a sense strand and an antisense strand, and the antisense strand comprises a region of at least near-perfect contiguous complementarity of at least 19 nucleotides to a target sequence of HIF1A mRNA, and the sense strand comprises a region of at least near-perfect contiguous identity of at least 19 nucleotides with a target sequence of HIF1A mRNA, respectively. In a further embodiment of the invention, the interfering RNA comprises a region of at least 13, 14, 15, 16, 17, or 18 contiguous nucleotides having percentages of sequence complementarity to or, having percentages of sequence identity with, the penultimate 13, 14, 15, 16, 17, or 18 nucleotides, respectively, of the 3' end of the corresponding target sequence within an mRNA.

The length of each strand of the interfering RNA comprises 19 to 49 nucleotides, and may comprise a length of 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides.

The antisense strand of an siRNA is the active guiding agent of the siRNA in that the antisense strand is incorporated into RISC, thus allowing RISC to identify target mRNAs with at least partial complementary to the antisense siRNA strand for cleavage or translational repression.

In embodiments of the present invention, interfering RNA target sequences (e.g., siRNA target sequences) within a target mRNA sequence are selected using available design tools. Interfering RNAs corresponding to a HIF1A target sequence are then tested by transfection of cells expressing the target mRNA followed by assessment of knockdown as described above.

Techniques for selecting target sequences for siRNAs are provided by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNA.

An embodiment of a 19-nucleotide DNA target sequence common to HIF1A variant 1 and HIV1A variant 2 is present at nucleotides 411 to 429 of SEQ ID NO:1:

```
                                              SEQ ID NO: 3
           5'-CAGTTGCCACTTCCACATA-3'.
```

An siRNA of the invention for targeting a corresponding mRNA sequence of SEQ ID NO:3 and having 21-nucleotide strands and a 2-nucleotide 3' overhang is:

```
                                              SEQ ID NO: 4
           5'-CAGUUGCCACUUCCACAUANN-3'

SEQ ID NO: 5
           3'-NNGUCAACGGUGAAGGUGUAU-5'.
```

Each "N" residue can be any nucleotide (A, C, G, U, T) or modified nucleotide. The 3' end can have a number of "N" residues between and including 1, 2, 3, 4, 5, and 6. The "N" residues on either strand can be the same residue (e.g., UU, AA, CC, GG, or TT) or they can be different (e.g., AC, AG, AU, CA, CG, CU, GA, GC, GU, UA, UC, or UG). The 3' overhangs can be the same or they can be different. In one embodiment, both strands have a 3'UU overhang.

An siRNA of the invention for targeting a corresponding mRNA sequence of SEQ ID NO:3 and having 21-nucleotide strands and a 3'UU overhang on each strand is:

```
                                                  SEQ ID NO: 6
           5'-CAGUUGCCACUUCCACAUAUU-3'

SEQ ID NO: 7
           3'-UUGUCAACGGUGAAGGUGUAU-5'.
```

The interfering RNA may also have a 5' overhang of nucleotides or it may have blunt ends. An siRNA of the invention for targeting a corresponding mRNA sequence of SEQ ID NO:3 and having 19-nucleotide strands and blunt ends is:

```
                                                  SEQ ID NO: 52
            5'-CAGUUGCCACUUCCACAUA-3'

SEQ ID NO: 53
            3'GUCAACGGUGAAGGUGUAU-5'.
```

The strands of a double-stranded interfering RNA (e.g., an siRNA) may be connected to form a hairpin or stem-loop structure (e.g., an shRNA). An shRNA of the invention targeting a corresponding mRNA sequence of SEQ ID NO:1 and having a 19 bp double-stranded stem region and a 3'UU overhang is:

```
                                                  SEQ ID NO: 8
                                      NNN
                                    /     \
             5'-CAGUUGCCACUUCCACAUA       N
             3'-UUGUCAACGGUGAAGGUGUAU     N.
                                    \     /
                                      NNN
```

N is a nucleotide A, T, C, G, U, or a modified form known by one of ordinary skill in the art. The number of nucleotides N in the loop is a number between and including 3 to 23, or 5 to 15, or 7 to 13, or 4 to 9, or 9 to 11, or the number of nucleotides N is 9. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) *Science* 296: 550) and 5'-UUUGUGUAG-3' (Castanotto, D. et al. (2002) *RNA* 8:1454). It will be recognized by one of skill in the art that the resulting single chain oligonucleotide forms a stem-loop or hairpin structure comprising a double-stranded region capable of interacting with the RNAi machinery.

The siRNA target sequence identified above can be extended at the 3' end to facilitate the design of dicer-substrate 27-mer duplexes. Extension of the 19-nucleotide DNA target sequence (SEQ ID NO:3) identified in the HIF1A DNA sequence (SEQ ID NO:1) by 6 nucleotides yields a 25-nucleotide DNA target sequence present at nucleotides 411 to 435 of SEQ ID NO:1:

```
                                                  SEQ ID NO: 54
           5'-CAGTTGCCACTTCCACATAATGTGA-3'.
```

A dicer-substrate 27-mer duplex of the invention for targeting a corresponding mRNA sequence of SEQ ID NO:54 is:

```
                                                  SEQ ID NO: 55
           5'-CAGUUGCCACUUCCACAUAAUGUGA-3'

SEQ ID NO: 56
           3'-UUGUCAACGGUGAAGGUGUAUUACACU-5'.
```

The two nucleotides at the 3' end of the sense strand (i.e., the GA nucleotides of SEQ ID NO:55) may be deoxynucleotides for enhanced processing. Design of dicer-substrate 27-mer duplexes from 19-21 nucleotide target sequences, such as provided herein, is further discussed by the Integrated DNA Technologies (IDT) website and by Kim, D.-H. et al., (February, 2005) *Nature Biotechnology* 23:2; 222-226.

When interfering RNAs are produced by chemical synthesis, phosphorylation at the 5' position of the nucleotide at the 5' end of one or both strands (when present) can enhance siRNA efficacy and specificity of the bound RISC complex but is not required since phosphorylation can occur intracellularly.

Table 1 lists examples of HIF1A variant 1 and variant 2 DNA target sequences of SEQ ID NO:1 and SEQ ID NO:2, respectively, from which siRNAs of the present invention are designed in a manner as set forth above. HIF1A encodes hypoxia-inducible factor 1 alpha, as noted above.

TABLE 1

| HIF1A Target Sequences for siRNAs | | |
|---|---|---|
| HIF1A variant 1 and variant 2 Target Sequences in Common | # of Starting Nucleotide with reference to SEQ ID NO: 1 | SEQ ID NO: |
| CAGTTGCCACTTCCACATA | 411 | 3 |
| TTGTTATGGTTCTCACAGA | 580 | 9 |
| TTATGGTTCTCACAGATGA | 583 | 10 |
| CAGGCCACATTCACGTATA | 868 | 11 |
| AGGCCACATTCACGTATAT | 869 | 12 |
| GCCGCTCAATTTATGAATA | 1099 | 13 |
| CCGCTCAATTTATGAATAT | 1100 | 14 |
| CAAGCAACTGTCATATATA | 1242 | 15 |
| TACGTTGTGAGTGGTATTA | 1302 | 16 |
| CCGGTTGAATCTTCAGATA | 1371 | 17 |
| TGACTCAGCTATTCACCAA | 1396 | 18 |
| TGAGGAAGTACCATTATAT | 1559 | 19 |
| GAGGAAGTACCATTATATA | 1560 | 20 |
| AGTTCACCTGAGCCTAATA | 1809 | 21 |
| GTATTCCAGCAGACTCAAA | 2085 | 22 |
| ATTCCAGCAGACTCAAATA | 2087 | 23 |
| ACAAGAACCTACTGCTAAT | 2105 | 24 |
| TGCCACCACTGATGAATTA | 2138 | 25 |
| CCATATAGAGATACTCAAA | 2256 | 26 |
| TCTGTCGCTTTGAGTCAAA | 2358 | 27 |

TABLE 1-continued

HIF1A Target Sequences for siRNAs

| | # of Starting Nucleotide with reference to SEQ ID NO: 1 | SEQ ID NO: |
|---|---|---|
| TGCAGAATGCTCAGAGAAA | 2422 | 28 |
| GGACACAGATTTAGACTTG | 1943 | 48 |
| GATGGAAGCACTAGACAAA | 1791 | 49 |
| CGTGTTATCTGTCGCTTTG | 2351 | 50 |
| TCACCAAAGTTGAATCAGA | 1408 | 51 |

| HIF1A variant 1 Target Sequence | # of Starting Nucleotide with reference to SEQ ID NO: 1 | SEQ ID NO: |
|---|---|---|
| GCAATCAATGGATGAAAGT | 2636 | 29 |
| GCTGACCAGTTATGATTGT | 2666 | 30 |
| GAGCTTTGGATCAAGTTAA | 2743 | 31 |
| TGGCTACAATACTGCACAA | 2858 | 32 |
| CTACAATACTGCACAAACT | 2861 | 33 |
| ATGATCATAGGCAGTTGAA | 3135 | 34 |
| CTATGTAGTTGTGGAAGTT | 3544 | 35 |
| GTGGAAGTTTATGCTAATA | 3554 | 36 |

| HIF1A variant 2 Target Sequence | # of Starting Nucleotide with reference to SEQ ID NO: 2 | SEQ ID NO: |
|---|---|---|
| TGTCGCTTTGAGTCAAAGA | 2360 | 37 |
| GATACTAGCTTTGCAGAAT | 2411 | 38 |
| TTTGCAGAATGCTCAGAGA | 2420 | 39 |
| ACAGCTGACCAGTTATGAT | 2536 | 40 |
| GCTGACCAGTTATGATTGT | 2539 | 41 |
| CAGTTATGATTGTGAAGTT | 2545 | 42 |
| GAGCTTTGGATCAAGTTAA | 2616 | 43 |
| TGGCTACAATACTGCACAA | 2731 | 44 |
| CTACAATACTGCACAAACT | 2734 | 45 |
| ATGATCATAGGCAGTTGAA | 3008 | 46 |
| GTGGAAGTTTATGCTAATA | 3427 | 47 |

As cited in the examples above, one of skill in the art is able to use the target sequence information provided in Table 1 to design interfering RNAs having a length shorter or longer than the sequences provided in the table and by referring to the sequence position in SEQ ID NO:1 or SEQ ID NO:2 and adding or deleting nucleotides complementary or near complementary to SEQ ID NO:1 or SEQ ID NO:2 respectively.

The target RNA cleavage reaction guided by siRNAs and other forms of interfering RNA is highly sequence specific. In general, siRNA containing a sense nucleotide strand identical in sequence to a portion of the target mRNA and an antisense nucleotide strand exactly complementary to a portion of the target mRNA are siRNA embodiments for inhibition of mRNAs cited herein. However, 100% sequence complementarity between the antisense siRNA strand and the target mRNA, or between the antisense siRNA strand and the sense siRNA strand, is not required to practice the present invention. Thus, for example, the invention allows for sequence variations that might be expected due to genetic mutation, strain polymorphism, or evolutionary divergence.

In one embodiment of the invention, the antisense strand of the siRNA has at least near-perfect contiguous complementarity of at least 19 nucleotides with the target mRNA. "Near-perfect," as used herein, means the antisense strand of the siRNA is "substantially complementary to," and the sense strand of the siRNA is "substantially identical to" at least a portion of the target mRNA. "Identity," as known by one of ordinary skill in the art, is the degree of sequence relatedness between nucleotide sequences as determined by matching the order and identity of nucleotides between the sequences. In one embodiment, the antisense strand of an siRNA having 80% and between 80% up to 100% complementarity, for example, 85%, 90% or 95% complementarity, to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to identify the greatest degree of matching of nucleotide sequences, for example, BLASTN (Altschul, S. F., et al. (1990) *J. Mol. Biol.* 215:403-410).

The term "percent identity" describes the percentage of contiguous nucleotides in a first nucleic acid molecule that is the same as in a set of contiguous nucleotides of the same length in a second nucleic acid molecule. The term "percent complementarity" describes the percentage of contiguous nucleotides in a first nucleic acid molecule that can base pair in the Watson-Crick sense with a set of contiguous nucleotides in a second nucleic acid molecule.

The relationship between a target mRNA (sense strand) and one strand of an siRNA (the sense strand) is that of identity. The sense strand of an siRNA is also called a passenger strand, if present. The relationship between a target mRNA (sense strand) and the other strand of an siRNA (the antisense strand) is that of complementarity. The antisense strand of an siRNA is also called a guide strand.

The penultimate base in a nucleic acid sequence that is written in a 5' to 3' direction is the next to the last base, i.e., the base next to the 3' base. The penultimate 13 bases of a nucleic acid sequence written in a 5' to 3' direction are the last 13 bases of a sequence next to the 3' base and not including the 3' base. Similarly, the penultimate 14, 15, 16, 17, or 18 bases of a nucleic acid sequence written in a 5' to 3' direction are the last 14, 15, 16, 17, or 18 bases of a sequence, respectively, next to the 3' base and not including the 3' base.

The phrase "a region of at least 13 contiguous nucleotides having at least 90% sequence complementarity to, or at least 90% sequence identity with, the penultimate 13 nucleotides of the 3' end of an mRNA corresponding to any one of (a sequence identifier)" allows a one nucleotide substitution. Two nucleotide substitutions (i.e., 11/13=85% identity/complementarity) are not included in such a phrase.

In one embodiment of the invention, the region of contiguous nucleotides is a region of at least 14 contiguous nucleotides having at least 85% sequence complementarity to, or at least 85% sequence identity with, the penultimate 14 nucleotides of the 3' end of an mRNA corresponding to the sequence identified by each sequence identifier. Two nucleotide substitutions (i.e., 12/14=86% identity/complementarity) are included in such a phrase.

In a further embodiment of the invention, the region of contiguous nucleotides is a region of at least 15, 16, 17, or 18 contiguous nucleotides having at least 80% sequence complementarity to, or at least 80% sequence identity with, the penultimate 14 nucleotides of the 3' end of an mRNA corresponding to the sequence of the sequence identifier. Three nucleotide substitutions are included in such a phrase.

The target sequence in the mRNAs corresponding to SEQ ID NO:1 or SEQ ID NO:2 may be in the 5' or 3' untranslated regions of the mRNA as well as in the coding region of the mRNA.

One or both of the strands of double-stranded interfering RNA may have a 3' overhang of from 1 to 6 nucleotides, which may be ribonucleotides or deoxyribonucleotides or a mixture thereof. The nucleotides of the overhang are not base-paired. In one embodiment of the invention, the interfering RNA comprises a 3' overhang of TT or UU. In another embodiment of the invention, the interfering RNA comprises at least one blunt end. The termini usually have a 5' phosphate group or a 3' hydroxyl group. In other embodiments, the antisense strand has a 5' phosphate group, and the sense strand has a 5' hydroxyl group. In still other embodiments, the termini are further modified by covalent addition of other molecules or functional groups.

The sense and antisense strands of the double-stranded siRNA may be in a duplex formation of two single strands as described above or may be a single molecule where the regions of complementarity are base-paired and are covalently linked by a hairpin loop so as to form a single strand. It is believed that the hairpin is cleaved intracellularly by a protein termed dicer to form an interfering RNA of two individual base-paired RNA molecules.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA. [0001] Further modifications include a 3' terminal biotin molecule, a peptide known to have cell-penetrating properties, a nanoparticle, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, or to direct localization or targeting.

There may be a region or regions of the antisense interfering RNA strand that is (are) not complementary to a portion of SEQ ID NO:1 or SEQ ID NO:2. Non-complementary regions may be at the 3', 5' or both ends of a complementary region or between two complementary regions.

Interfering RNAs may be generated exogenously by chemical synthesis, by in vitro transcription, or by cleavage of longer double-stranded RNA with dicer or another appropriate nuclease with similar activity. Chemically synthesized interfering RNAs, produced from protected ribonucleoside phosphoramidites using a conventional DNA/RNA synthesizer, may be obtained from commercial suppliers such as Ambion Inc. (Austin, Tex.), Invitrogen (Carlsbad, Calif.), or Dharmacon (Lafayette, Colo.). Interfering RNAs are purified by extraction with a solvent or resin, precipitation, electrophoresis, chromatography, or a combination thereof, for example. Alternatively, interfering RNA may be used with little if any purification to avoid losses due to sample processing.

Interfering RNAs can also be expressed endogenously from plasmid or viral expression vectors or from minimal expression cassettes, for example, PCR generated fragments comprising one or more promoters and an appropriate template or templates for the interfering RNA. Examples of commercially available plasmid-based expression vectors for shRNA include members of the pSilencer series (Ambion, Austin, Tex.) and pCpG-siRNA (InvivoGen, San Diego, Calif.). Viral vectors for expression of interfering RNA may be derived from a variety of viruses including adenovirus, adeno-associated virus, lentivirus (e.g., HIV, FIV, and EIAV), and herpes virus. Examples of commercially available viral vectors for shRNA expression include pSilencer adeno (Ambion, Austin, Tex.) and pLenti6/BLOCK-iT™-DEST (Invitrogen, Carlsbad, Calif.). Selection of viral vectors, methods for expressing the interfering RNA from the vector and methods of delivering the viral vector are within the ordinary skill of one in the art. Examples of kits for production of PCR-generated shRNA expression cassettes include Silencer Express (Ambion, Austin, Tex.) and siXpress (Minis, Madison, Wis.). A first interfering RNA may be administered via in vivo expression from a first expression vector capable of expressing the first interfering RNA and a second interfering RNA may be administered via in vivo expression from a second expression vector capable of expressing the second interfering RNA, or both interfering RNAs may be administered via in vivo expression from a single expression vector capable of expressing both interfering RNAs.

Interfering RNAs may be expressed from a variety of eukaryotic promoters known to those of ordinary skill in the art, including pol III promoters, such as the U6 or H1 promoters, or pol II promoters, such as the cytomegalovirus promoter. Those of skill in the art will recognize that these promoters can also be adapted to allow inducible expression of the interfering RNA.

Hybridization Under Physiological Conditions:

In certain embodiments of the present invention, an antisense strand of an interfering RNA hybridizes with an mRNA in vivo as part of the RISC complex.

"Hybridization" refers to a process in which single-stranded nucleic acids with complementary or near-complementary base sequences interact to form hydrogen-bonded complexes called hybrids. Hybridization reactions are sensitive and selective. In vitro, the specificity of hybridization (i.e., stringency) is controlled by the concentrations of salt or formamide in prehybridization and hybridization solutions, for example, and by the hybridization temperature; such procedures are well known in the art. In particular, stringency is increased by reducing the concentration of salt, increasing the concentration of formamide, or raising the hybridization temperature.

For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, *Molecular Cloning: A Laboratory Manual*, Cold Spring Harbor Laboratory Press, Cold Spring Harbor, N.Y. Further examples of stringent hybridization conditions include 400 mM NaCl, 40 mM PIPES pH 6.4, 1 mM EDTA, 50° C. or 70° C. for 12-16 hours followed by washing, or hybridization at 70° C. in 1×SSC or 50° C. in 1×SSC, 50% formamide followed by washing at 70° C. in 0.3×SSC, or hybridization at 70° C. in 4×SSC or 50° C. in 4×SSC, 50% formamide followed by washing at 67° C. in 1×SSC. The temperature for hybridization is about 5-10° C. less than the melting temperature ($T_m$) of the hybrid where $T_m$ is determined for hybrids between 19 and 49 base pairs in length using the following calculation: $T_m° C.=81.5+16.6(\log_{10}[Na+])+0.41$ (% G+C)−(600/N) where N is the number of bases in the hybrid, and [Na+] is the concentration of sodium ions in the hybridization buffer.

The above-described in vitro hybridization assay provides a method of predicting whether binding between a candidate siRNA and a target will have specificity. However, in the context of the RISC complex, specific cleavage of a target can also occur with an antisense strand that does not demonstrate high stringency for hybridization in vitro.

Single-Stranded Interfering RNA:

As cited above, interfering RNAs ultimately function as single strands. Single-stranded (ss) interfering RNA has been found to effect mRNA silencing, albeit less efficiently than double-stranded siRNA. Therefore, embodiments of the present invention also provide for administration of a ss interfering RNA that hybridizes under physiological conditions to a portion of SEQ ID NO:1 or SEQ ID NO:2 and has a region of at least near-perfect contiguous complementarity of at least 19 nucleotides with the hybridizing portion of SEQ ID NO:1 or SEQ ID NO:2, respectively. The ss interfering RNA has a length of 19 to 49 nucleotides as for the ds siRNA cited above. The ss interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

SS interfering RNAs are synthesized chemically or by in vitro transcription or expressed endogenously from vectors or expression cassettes as for ds interfering RNAs. 5' Phosphate groups may be added via a kinase, or a 5' phosphate may be the result of nuclease cleavage of an RNA. Delivery is as for ds interfering RNAs. In one embodiment, ss interfering RNAs having protected ends and nuclease resistant modifications are administered for silencing. SS interfering RNAs may be dried for storage or dissolved in an aqueous solution. The solution may contain buffers or salts to inhibit annealing or for stabilization.

Hairpin Interfering RNA:

A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Mode of Administration:

Interfering RNA may be delivered via aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal administration, for example.

Interfering RNA may be delivered directly to the eye by ocular tissue injection such as periocular, conjunctival, subtenon, intracameral, intravitreal, intraocular, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

Subject:

A subject in need of treatment for ocular angiogenesis or at risk for developing ocular angiogenesis is a human or other mammal having ocular angiogenesis or at risk of having ocular angiogenesis associated with undesired or inappropriate expression or activity of HIF1A as cited herein. Ocular structures associated with such disorders may include the eye, retina, choroid, lens, cornea, trabecular meshwork, iris, optic nerve, optic nerve head, sclera, anterior or posterior segments, or ciliary body, for example. A subject may also be an ocular cell, cell culture, organ or an ex vivo organ or tissue.

Formulations and Dosage:

Pharmaceutical formulations comprise interfering RNAs, or salts thereof, of the invention up to 99% by weight mixed with a physiologically acceptable carrier medium such as water, buffer, saline, glycine, hyaluronic acid, mannitol, and the like.

Interfering RNAs of the present invention are administered as solutions, suspensions, or emulsions. The following are examples of possible formulations embodied by this invention.

| | Amount in weight % |
|---|---|
| Interfering RNA | up to 99; 0.1-99; 0.1-50; 0.5-10.0 |
| Hydroxypropylmethylcellulose | 0.5 |
| Sodium chloride | 0.8 |
| Benzalkonium Chloride | 0.01 |
| EDTA | 0.01 |
| NaOH/HCl | qs pH 7.4 |
| Purified water (RNase-free) | qs 100 mL |

| | Amount in weight % |
|---|---|
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water (RNase-free) | q.s. to 100% |

| | Amount in weight % |
|---|---|
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |
| Cremophor EL | 0.1 |
| Benzalkonium chloride | 0.01 |
| HCl and/or NaOH | pH 7.3-7.4 |
| Purified water (RNase-free) | q.s. to 100% |

| | Amount in weight % |
|---|---|
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water (RNase-free) | q.s. to 100% |

Generally, an effective amount of the interfering RNAs of embodiments of the invention results in an extracellular concentration at the surface of the target cell of from 100 pM to 1 μM, or from 1 nM to 100 nM, or from 5 nM to about 50 nM, or to about 25 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions are delivered to the surface of the target organ one to four times per day, or on an extended delivery schedule such as daily, weekly, bi-weekly, monthly, or longer, according to the routine discretion of a skilled clinician. The pH of the formulation is about pH 4-9, or pH 4.5 to pH 7.4.

Therapeutic treatment of patients with interfering RNAs directed against HIF1A mRNA is expected to be beneficial over small molecule treatments by increasing the duration of action, thereby allowing less frequent dosing and greater patient compliance.

An effective amount of a formulation may depend on factors such as the age, race, and sex of the subject, the severity of the ocular angiogenesis, the rate of target gene transcript/protein turnover, the interfering RNA potency, and the interfering RNA stability, for example. In one embodiment, the interfering RNA is delivered topically to a target organ and reaches the HIF1A-containing tissue such as the retina or optic nerve head at a therapeutic dose thereby ameliorating an ocular angiogenesis-associated disease process.

Acceptable Carriers:

An acceptable carrier refers to those carriers that cause at most, little to no ocular irritation, provide suitable preservation if needed, and deliver one or more interfering RNAs of the present invention in a homogenous dosage. An acceptable carrier for administration of interfering RNA of embodiments of the present invention include the cationic lipid-based transfection reagents TransIT®-TKO (Minis Corporation, Madison, Wis.), LIPOFECTIN®, Lipofectamine, OLIGOFECTAMINE™ (Invitrogen, Carlsbad, Calif.), or DHARMAFECT™ (Dharmacon, Lafayette, Colo.); polycations such as polyethyleneimine; cationic peptides such as Tat, polyarginine, or Penetratin (Antp peptide); or liposomes. Liposomes are formed from standard vesicle-forming lipids and a sterol, such as cholesterol, and may include a targeting molecule such as a monoclonal antibody having binding affinity for endothelial cell surface antigens, for example. Further, the liposomes may be PEGylated liposomes.

The interfering RNAs may be delivered in solution, in suspension, or in bioerodible or non-bioerodible delivery devices. The interfering RNAs can be delivered alone or as components of defined, covalent conjugates. The interfering RNAs can also be complexed with cationic lipids, cationic peptides, or cationic polymers; complexed with proteins, fusion proteins, or protein domains with nucleic acid binding properties (e.g., protamine); or encapsulated in nanoparticles or liposomes. Tissue- or cell-specific delivery can be accomplished by the inclusion of an appropriate targeting moiety such as an antibody or antibody fragment.

For ophthalmic delivery, an interfering RNA may be combined with ophthalmologically acceptable preservatives, co-solvents, surfactants, viscosity enhancers, penetration enhancers, buffers, sodium chloride, or water to form an aqueous, sterile ophthalmic suspension or solution. Solution formulations may be prepared by dissolving the interfering RNA in a physiologically acceptable isotonic aqueous buffer. Further, the solution may include an acceptable surfactant to assist in dissolving the inhibitor. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ophthalmic ointment formulation, the interfering RNA is combined with a preservative in an appropriate vehicle, such as mineral oil, liquid lanolin, or white petrolatum. Sterile ophthalmic gel formulations may be prepared by suspending the interfering RNA in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the interfering RNA is less penetrating in the eye.

Kits:

Embodiments of the present invention provide a kit that includes reagents for attenuating the expression of an mRNA as cited herein in a cell. The kit contains an siRNA or an shRNA expression vector. For siRNAs and non-viral shRNA expression vectors the kit also contains a transfection reagent or other suitable delivery vehicle. For viral shRNA expression vectors, the kit may contain the viral vector and/or the necessary components for viral vector production (e.g., a packaging cell line as well as a vector comprising the viral vector template and additional helper vectors for packaging). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and an acceptable carrier. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The ability of interfering RNA to knock-down the levels of endogenous target gene expression in, for example, a human ocular cell line is evaluated in vitro as follows. Transformed human cells are plated 24 h prior to transfection in standard growth medium (e.g., DMEM supplemented with 10% fetal bovine serum). Transfection is performed using Dharmafect 1 (Dharmacon, Lafayette, Colo.) according to the manufacturer's instructions at interfering RNA concentrations ranging from 0.1 nM-100 nM. Non-targeting control siRNA and lamin A/C siRNA (Dharmacon) are used as controls. Target mRNA levels are assessed by qPCR 24 h post-transfection using, for example, TAQMAN® forward and reverse primers and a probe set that encompasses the target site (Applied Biosystems, Foster City, Calif.). Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of interfering RNA should be used that will produce the desired level of knock-down in target gene expression.

The ability of interfering RNAs of the present invention to knock-down levels of HIF1A protein expression is further exemplified in Example 1 as follows.

Example 1

Interfering RNA for Specifically Silencing HIF1A

The present study examines the ability of HIF1A-interfering RNA to knock down the levels of endogenous HIF-1α protein expression in cultured HeLa cells.

Transfection of HeLa cells was accomplished using standard in vitro concentrations (0.1-10 nM) of HIF1A siRNAs, siCONTROL RISC-free siRNA #1, or siCONTROL Non-targeting siRNA #2 (NTC2) and DHARMAFECT® #1 transfection reagent (Dharmacon, Lafayette, Colo.). All siRNAs were dissolved in 1× siRNA buffer, an aqueous solution of 20 mM KCl, 6 mM HEPES (pH 7.5), 0.2 mM $MgCl_2$. Control samples included a buffer control in which the volume of siRNA was replaced with an equal volume of 1× siRNA buffer (−siRNA). Forty-eight hours after transfection, the cells were treated with 100 μM $CoCl_2$ for 4 h to induce HIF-1α protein expression, and western blots were performed to assess HIF-1α level. The HIF1A siRNAs are double-stranded interfering RNAs having specificity for the following targets: siHIF1A #1 targets SEQ ID NO:48; siHIF1A #3 targets SEQ ID NO:49; siHIF1A #5 targets SEQ ID NO:50; siHIF1A #6 targets SEQ ID NO:51. As shown by the data of the FIGURE, each of the four HIF1A siRNAs reduced HIF-1α protein expression significantly at 10 nM relative to the control siRNAs. However, siHIF1A #3 and siHIF1A #6 also silenced HIF-1α protein expression significantly at 0.1 nM, indicating that these HIF1A siRNAs are particularly effective relative to siHIF1A #1 and siHIF1A #5.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

What is claimed is:

1. A pharmaceutical composition comprising: an interfering RNA that contains one or more chemically modified nucleotides, one or more deoxyribonucleotides, and/or one or more non-phosphodiester linkages, and a pharmaceutically acceptable carrier, wherein the interfering RNA has a sense strand and an antisense strand, wherein each strand is 19-49 nucleotides in length, and wherein the sense strand comprises the RNA sequence corresponding to SEQ ID NO: 11, wherein the interfering RNA inhibits HIF1A.

2. The pharmaceutical composition of claim 1 wherein the interfering RNA is an shRNA, siRNA, or miRNA.

* * * * *

SEQUENCE LISTING

```
<160> NUMBER OF SEQ ID NOS: 56

<210> SEQ ID NO 1
<211> LENGTH: 3958
<212> TYPE: DNA
<213> ORGANISM: Homo sapiens

<400> SEQUENCE: 1
gtgctgcctc gtctgagggg acaggaggat caccctcttc gtcgcttcgg ccagtgtgtc      60
gggctgggcc ctgacaagcc acctgaggag aggctcggag ccgggcccgg accccggcga     120
ttgccgcccg cttctctcta gtctcacgag gggtttcccg cctcgcaccc ccacctctgg     180
acttgccttt ccttctcttc tccgcgtgtg gagggagcca gcgcttaggc cggagcgagc     240
ctgggggccg cccgccgtga agacatcgcg gggaccgatt caccatggag ggcgccggcg     300
gcgcgaacga caagaaaaag ataagttctg aacgtcgaaa agaaaagtct cgagatgcag     360
ccagatctcg gcgaagtaaa gaatctgaag tttttttatga gcttgctcat cagttgccac     420
ttccacataa tgtgagttcg catcttgata aggcctctgt gatgaggctt accatcagct     480
atttgcgtgt gaggaaactt ctggatgctg gtgatttgga tattgaagat gacatgaaag     540
```

```
cacagatgaa ttgcttttat ttgaaagcct tggatggttt tgttatggtt ctcacagatg    600
atggtgacat gatttacatt tctgataatg tgaacaaata catgggatta actcagtttg    660
aactaactgg acacagtgtg tttgatttta ctcatccatg tgaccatgag gaaatgagag    720
aaatgcttac acacagaaat ggccttgtga aaaagggtaa agaacaaaac acacagcgaa    780
gcttttttct cagaatgaag tgtaccctaa ctagccgagg aagaactatg aacataaagt    840
ctgcaacatg gaaggtattg cactgcacag gccacattca cgtatatgat accaacagta    900
accaacctca gtgtgggtat aagaaaccac ctatgacctg cttggtgctg atttgtgaac    960
ccattcctca cccatcaaat attgaaattc ctttagatag caagactttc ctcagtcgac   1020
acagcctgga tatgaaattt tcttattgtg atgaaagaat taccgaattg atgggatatg   1080
agccagaaga acttttaggc cgctcaattt atgaatatta tcatgctttg gactctgatc   1140
atctgaccaa aactcatcat gatatgttta ctaaaggaca agtcaccaca ggacagtaca   1200
ggatgcttgc caaagaggt ggatatgtct gggttaaaac tcaagcaact gtcatatata    1260
acaccaagaa ttctcaacca cagtgcattg tatgtgtgaa ttacgttgtg agtggtatta   1320
ttcagcacga cttgattttc tcccttcaac aaacagaatg tgtccttaaa ccggttgaat   1380
cttcagatat gaaatgact cagctattca ccaaagttga atcagaagat acaagtagcc   1440
tctttgacaa acttaagaag gaacctgatg ctttaacttt gctggcccca gccgctggag   1500
acacaatcat atctttagat tttggcagca acgacacaga aactgatgac cagcaacttg   1560
aggaagtacc attatataat gatgtaatgc tcccctcacc caacgaaaaa ttacagaata   1620
taaatttggc aatgtctcca ttacccaccg ctgaaacgcc aaagccactt cgaagtagtg   1680
ctgaccctgc actcaatcaa gaagttgcat taaaattaga accaaatcca gagtcactgg   1740 aacttttcttt taccatgccc cagattcagg atcagacacc tagtccttcc gatggaagca   1800
ctagacaaag ttcacctgag cctaatagtc ccagtgaata ttgtttttat gtggatagtg   1860
atatggtcaa tgaattcaag ttggaattgg tagaaaaact ttttgctgaa gacacagaag   1920
caaagaaccc attttctact caggacacag atttagactt ggagatgtta gctccctata   1980
tcccaatgga tgatgacttc cagttacgtt ccttcgatca gttgtcacca ttagaaagca   2040
gttccgcaag ccctgaaagc gcaagtcctc aaagcacagt tacagtattc cagcagactc   2100
aaatacaaga acctactgct aatgccacca ctaccactgc caccactgat gaattaaaaa   2160
cagtgacaaa agaccgtatg gaagacatta aatattgat tgcatctcca tctcctaccc   2220
acatacataa agaaactact agtgccacat catcaccata tagagatact caaagtcgga   2280
cagcctcacc aaacagagca ggaaaaggag tcatagaaca gacagaaaaa tctcatccaa   2340
gaagccctaa cgtgttatct gtcgcttttga gtcaaagaac tacagttcct gaggaagaac   2400
taaatccaaa gatactagct ttgcagaatg ctcagagaaa gcgaaaaatg gaacatgatg   2460
gttcactttt tcaagcagta ggaattggaa cattattaca gcagccagac gatcatgcag   2520
ctactacatc acttttcttgg aaacgtgtaa aaggatgcaa atcagtgaa cagaatggaa   2580 tggagcaaaa gacaattatt ttaataccct ctgatttagc atgtagactg ctggggcaat   2640
caatggatga aagtggatta ccacagctga ccagttatga ttgtgaagtt aatgctccta   2700
tacaaggcag cagaaaccta ctgcagggtg aagaattact cagagctttg gatcaagtta   2760
actgagcttt tcttaatttt cattcctttt tttggacact ggtggctcac tacctaaagc   2820 agtctatttta tatttctac atctaatttt agaagcctgg ctacaatact gcacaaactt   2880
```

| | |
|---|---:|
| ggttagttca attttttgatc cccttttctac ttaatttaca ttaatgctct tttttagtat | 2940 |
| gttctttaat gctggatcac agacagctca ttttctcagt tttttggtat ttaaaccatt | 3000 |
| gcattgcagt agcatcattt taaaaaatgc acctttttat ttatttattt ttggctaggg | 3060 |
| agtttatccc ttttttcgaat tattttttaag aagatgccaa tataatttt gtaagaaggc | 3120 |
| agtaaccttt catcatgatc ataggcagtt gaaaaatttt tacacctttt ttttcacatt | 3180 |
| ttacataaat aataatgctt tgccagcagt acgtggtagc cacaattgca caatatattt | 3240 |
| tcttaaaaaa taccagcagt tactcatgga atatattctg cgtttataaa actagttttt | 3300 |
| aagaagaaat ttttttttggc ctatgaaatt gttaaacctg gaacatgaca ttgttaatca | 3360 |
| tataataatg attcttaaat gctgtatggt ttattattta aatgggtaaa gccatttaca | 3420 |
| taatatagaa agatatgcat atatctagaa ggtatgtggc attatttgg ataaaattct | 3480 |
| caattcagag aaatcatctg atgtttctat agtcactttg ccagctcaaa agaaaacaat | 3540 |
| accctatgta gttgtggaag tttatgctaa tattgtgtaa ctgatattaa acctaaatgt | 3600 |
| tctgcctacc ctgttggtat aaagatattt tgagcagact gtaaacaaga aaaaaaaat | 3660 |
| catgcattct tagcaaaatt gcctagtatg ttaatttgct caaaatacaa tgtttgattt | 3720 |
| tatgcacttt gtcgctatta acatccttt tttcatgtag atttcaataa ttgagtaatt | 3780 |
| ttagaagcat tattttagga atatatagtt gtcacagtaa atatcttgtt ttttctatgt | 3840 |
| acattgtaca aatttttcat tcctttttgct ctttgtggtt ggatctaaca ctaactgtat | 3900 |
| tgttttgtta catcaaataa acatcttctg tggaccagga aaaaaaaaaa aaaaaaa | 3958 |

<210> SEQ ID NO 2
<211> LENGTH: 3812
<212> TYPE: DNA
<213> ORGANISM: Homo sapiens

<400> SEQUENCE: 2

| | |
|---|---:|
| gtgctgcctc gtctgagggg acaggaggat caccctcttc gtcgcttcgg ccagtgtgtc | 60 |
| gggctgggcc ctgacaagcc acctgaggag aggctcggag ccgggcccgg accccggcga | 120 |
| tgccgcccg cttctctcta gtctcacgag gggtttcccg cctcgcaccc ccacctctgg | 180 |
| acttgccttt ccttctcttc tccgcgtgtg gagggagcca gcgcttaggc cggagcgagc | 240 |
| ctggggggccg cccgccgtga agacatcgcg gggaccgatt caccatggag ggcgccggcg | 300 |
| gcgcgaacga caagaaaaag ataagttctg aacgtcgaaa agaaaagtct cgagatgcag | 360 |
| ccagatctcg gcgaagtaaa gaatctgaag ttttttatga gcttgctcat cagttgccac | 420 |
| ttccacataa tgtgagttcg catcttgata aggcctctgt gatgaggctt accatcagct | 480 |
| atttgcgtgt gaggaaactt ctggatgctg gtgatttgga tattgaagat gacatgaaag | 540 |
| cacagatgaa ttgcttttat ttgaaagcct tggatggttt tgttatggtt ctcacagatg | 600 |
| atggtgacat gatttacatt tctgataatg tgaacaaata catgggatta actcagtttg | 660 |
| aactaactgg acacagtgtg tttgattta ctcatccatg tgaccatgag gaaatgagag | 720 |
| aaatgcttac acacagaaat ggccttgtga aaagggtaa agaacaaaac acacagcgaa | 780 |
| gctttttttct cagaatgaag tgtacccctaa ctagccgagg aagaactatg aacataaagt | 840 |
| ctgcaacatg gaaggtattg cactgcacag gccacattca cgtatatgat accaacagta | 900 |
| accaacctca gtgtgggtat aagaaaccac ctatgacctg cttggtgctg atttgtgaac | 960 |
| ccattcctca cccatcaaat attgaaattc ctttagatag caagactttc ctcagtcgac | 1020 |
| acagcctgga tatgaaattt tcttattgtg atgaaagaat taccgaattg atgggatatg | 1080 |

```
agccagaaga acttttaggc cgctcaattt atgaatatta tcatgctttg gactctgatc    1140
atctgaccaa aactcatcat gatatgttta ctaaaggaca agtcaccaca ggacagtaca    1200
ggatgcttgc caaagaggt ggatatgtct gggttgaaac tcaagcaact gtcatatata     1260
acaccaagaa ttctcaacca cagtgcattg tatgtgtgaa ttacgttgtg agtggtatta    1320
ttcagcacga cttgattttc tcccttcaac aaacagaatg tgtccttaaa ccggttgaat    1380
cttcagatat gaaaatgact cagctattca ccaaagttga atcagaagat acaagtagcc    1440
tctttgacaa acttaagaag gaacctgatg ctttaacttt gctggcccca gccgctggag    1500
acacaatcat atctttagat tttggcagca acgacacaga aactgatgac cagcaacttg    1560
aggaagtacc attatataat gatgtaatgc tcccctcacc caacgaaaaa ttacagaata    1620
taaatttggc aatgtctcca ttacccaccg ctgaaacgcc aaagccactt cgaagtagtg    1680
ctgaccctgc actcaatcaa gaagttgcat taaaattaga accaaatcca gagtcactgg    1740
aactttcttt taccatgccc cagattcagg atcagacacc tagtccttcc gatggaagca    1800
ctagacaaag ttcacctgag cctaatagtc ccagtgaata ttgttttat gtggatagtg     1860 atatggtcaa tgaattcaag ttggaattgg tagaaaaact ttttgctgaa gacacagaag    1920
caaagaaccc attttctact caggacacag atttagactt ggagatgtta gctccctata    1980
tcccaatgga tgatgacttc cagttacgtt ccttcgatca gttgtcacca ttagaaagca    2040
gttccgcaag ccctgaaagc gcaagtcctc aaagcacagt tacagtattc cagcagactc    2100
aaatacaaga acctactgct aatgccacca ctaccactgc caccactgat gaattaaaaa    2160
cagtgacaaa agaccgtatg gaagacatta aaatattgat tgcatctcca tctcctaccc    2220
acatacataa agaaactact agtgccacat catcaccata tagagatact caaagtcgga    2280
cagcctcacc aaacagagca ggaaaaggag tcatagaaca gacagaaaaa tctcatccaa    2340
gaagccctaa cgtgttatct gtcgctttga gtcaaagaac tacagttcct gaggaagaac    2400
taaatccaaa gatactagct ttgcagaatg ctcagagaaa gcgaaaaatg gaacatgatg    2460
gttcactttt tcaagcagta ggaattattt agcatgtaga ctgctggggc aatcaatgga    2520
tgaaagtgga ttaccacagc tgaccagtta tgattgtgaa gttaatgctc ctatacaagg    2580
cagcagaaac ctactgcagg gtgaagaatt actcagagct ttggatcaag ttaactgagc    2640
ttttctttaa tttcattcct ttttttggac actggtggct cactacctaa agcagtctat    2700
ttatattttc tacatctaat tttagaagcc tggctacaat actgcacaaa cttggttagt    2760
tcaatttttg atcccctttc tacttaattt acattaatgc tctttttag tatgttcttt     2820 aatgctggat cacagacagc tcattttctc agttttttgg tatttaaacc attgcattgc    2880
agtagcatca ttttaaaaaa tgcacctttt tattattta ttttggcta gggagtttat      2940 cccttttcg aattattttt aagaagatgc caatataatt tttgtaagaa ggcagtaacc     3000
tttcatcatg atcataggca gttgaaaaat ttttacacct ttttttttcac attttacata    3060 aataataatg ctttgccagc agtacgtggt agccacaatt gcacaatata ttttcttaaa    3120
aaataccagc agttactcat ggaatatatt ctgcgtttat aaaactagtt tttaagaaga    3180
aatttttttt ggcctatgaa attgttaaac ctggaacatg acattgttaa tcatataata    3240
atgattctta aatgctgtat ggtttattat ttaaatgggt aaagccattt acataatata    3300
gaaagatatg catatatcta gaaggtatgt ggcattatt tggataaaat tctcaattca     3360
gagaaatcat ctgatgtttc tatagtcact ttgccagctc aaaagaaaac aatacctat    3420
```

-continued

```
gtagttgtgg aagtttatgc taatattgtg taactgatat taaacctaaa tgttctgcct      3480
accctgttgg tataaagata ttttgagcag actgtaaaca agaaaaaaaa aatcatgcat      3540
tcttagcaaa attgcctagt atgttaattt gctcaaaata caatgtttga ttttatgcac      3600
tttgtcgcta ttaacatcct ttttttcatg tagatttcaa taattgagta attttagaag      3660
cattatttta ggaatatata gttgtcacag taaatatctt gttttttcta tgtacattgt      3720
acaaattttt cattccttttt gctctttgtg gttggatcta acactaactg tattgttttg      3780
ttacatcaaa taaacatctt ctgtggacca gg                                    3812
```

```
<210> SEQ ID NO 3
<211> LENGTH: 19
<212> TYPE: DNA
<213> ORGANISM: Artificial
<220> FEATURE:
<223> OTHER INFORMATION: Target Sequence

<400> SEQUENCE: 3
cagttgccac ttccacata                                                    19

<210> SEQ ID NO 4
<211> LENGTH: 21
<212> TYPE: DNA
<213> ORGANISM: Artificial
<220> FEATURE:
<223> OTHER INFORMATION: sense strand with 3'NN
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: any, A, T/U, C, G

<400> SEQUENCE: 4
caguugccac uuccacauan n                                                 21

<210> SEQ ID NO 5
<211> LENGTH: 21
<212> TYPE: DNA
<213> ORGANISM: Artificial
<220> FEATURE:
<223> OTHER INFORMATION: Antisense strand with 3'NN
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: any, A, T/U, C, G

<400> SEQUENCE: 5
uauguggaag uggcaacugn n                                                 21

<210> SEQ ID NO 6
<211> LENGTH: 21
<212> TYPE: RNA
<213> ORGANISM: Artificial
<220> FEATURE:
<223> OTHER INFORMATION: Sense Strand

<400> SEQUENCE: 6
caguugccac uuccacauau u                                                 21
```

```
<210> SEQ ID NO 7
<211> LENGTH: 21
<212> TYPE: RNA
<213> ORGANISM: Artificial
<220> FEATURE:
<223> OTHER INFORMATION: Antisense Strand

<400> SEQUENCE: 7
uauguggaag uggcaacugu u                                              21

<210> SEQ ID NO 8
<211> LENGTH: 48
<212> TYPE: DNA
<213> ORGANISM: Artificial
<220> FEATURE:
<223> OTHER INFORMATION: Hairpin duplex with loop
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(27)
<223> OTHER INFORMATION: any, A, T/U, C, G
<220> FEATURE:
<221> NAME/KEY: misc_feature
<222> LOCATION: (28)..(48)
<223> OTHER INFORMATION: ribonucleotides

<400> SEQUENCE: 8
caguugccac uuccacauan nnnnnnnuau guggaagugg caacuguu                 48

<210> SEQ ID NO 9
<211> LENGTH: 19
<212> TYPE: DNA
<213> ORGANISM: Artificial
<220> FEATURE:
<223> OTHER INFORMATION: Target Sequence

<400> SEQUENCE: 9
ttgttatggt tctcacaga                                                 19

<210> SEQ ID NO 10
<211> LENGTH: 19
<212> TYPE: DNA
<213> ORGANISM: Artificial
<220> FEATURE:
<223> OTHER INFORMATION: Target Sequence

<400> SEQUENCE: 10
ttatggttct cacagatga                                                 19

<210> SEQ ID NO 11
<211> LENGTH: 19
<212> TYPE: DNA
<213> ORGANISM: Artificial
<220> FEATURE:
<223> OTHER INFORMATION: Target Sequence

<400> SEQUENCE: 11
caggccacat tcacgtata                                                 19

<210> SEQ ID NO 12
<211> LENGTH: 19
<212> TYPE: DNA
<213> ORGANISM: Artificial
<220> FEATURE:
<223> OTHER INFORMATION: Target Sequence
```

```
<400> SEQUENCE: 12
aggccacatt cacgtatat                                                19

<210> SEQ ID NO 13
<211> LENGTH: 19
<212> TYPE: DNA
<213> ORGANISM: Artificial
<220> FEATURE:
<223> OTHER INFORMATION: Target Sequence

<400> SEQUENCE: 13
gccgctcaat ttatgaata                                                19

<210> SEQ ID NO 14
<211> LENGTH: 19
<212> TYPE: DNA
<213> ORGANISM: Artificial
<220> FEATURE:
<223> OTHER INFORMATION: Target Sequence

<400> SEQUENCE: 14
ccgctcaatt tatgaatat                                                19

<210> SEQ ID NO 15
<211> LENGTH: 19
<212> TYPE: DNA
<213> ORGANISM: Artificial
<220> FEATURE:
<223> OTHER INFORMATION: Target Sequence

<400> SEQUENCE: 15
caagcaactg tcatatata                                                19

<210> SEQ ID NO 16
<211> LENGTH: 19
<212> TYPE: DNA
<213> ORGANISM: Artificial
<220> FEATURE:
<223> OTHER INFORMATION: Target Sequence

<400> SEQUENCE: 16
tacgttgtga gtggtatta                                                19

<210> SEQ ID NO 17
<211> LENGTH: 19
<212> TYPE: DNA
<213> ORGANISM: Artificial
<220> FEATURE:
<223> OTHER INFORMATION: Target Sequence

<400> SEQUENCE: 17
ccggttgaat cttcagata                                                19

<210> SEQ ID NO 18
<211> LENGTH: 19
<212> TYPE: DNA
<213> ORGANISM: Artificial
<220> FEATURE:
<223> OTHER INFORMATION: Target Sequence

<400> SEQUENCE: 18
tgactcagct attcaccaa                                                19

<210> SEQ ID NO 19
<211> LENGTH: 19
```

```
<212> TYPE: DNA
<213> ORGANISM: Artificial
<220> FEATURE:
<223> OTHER INFORMATION: Target Sequence

<400> SEQUENCE: 19
tgaggaagta ccattatat                                                   19

<210> SEQ ID NO 20
<211> LENGTH: 19
<212> TYPE: DNA
<213> ORGANISM: Artificial
<220> FEATURE:
<223> OTHER INFORMATION: Target Sequence

<400> SEQUENCE: 20
gaggaagtac cattatata                                                   19

<210> SEQ ID NO 21
<211> LENGTH: 19
<212> TYPE: DNA
<213> ORGANISM: Artificial
<220> FEATURE:
<223> OTHER INFORMATION: Target Sequence

<400> SEQUENCE: 21
agttcacctg agcctaata                                                   19

<210> SEQ ID NO 22
<211> LENGTH: 19
<212> TYPE: DNA
<213> ORGANISM: Artificial
<220> FEATURE:
<223> OTHER INFORMATION: Target Sequence

<400> SEQUENCE: 22
gtattccagc agactcaaa                                                   19

<210> SEQ ID NO 23
<211> LENGTH: 19
<212> TYPE: DNA
<213> ORGANISM: Artificial
<220> FEATURE:
<223> OTHER INFORMATION: Target Sequence

<400> SEQUENCE: 23
attccagcag actcaaata                                                   19

<210> SEQ ID NO 24
<211> LENGTH: 19
<212> TYPE: DNA
<213> ORGANISM: Artificial
<220> FEATURE:
<223> OTHER INFORMATION: Target Sequence

<400> SEQUENCE: 24
acaagaacct actgctaat                                                   19

<210> SEQ ID NO 25
<211> LENGTH: 19
<212> TYPE: DNA
<213> ORGANISM: Artificial
<220> FEATURE:
<223> OTHER INFORMATION: Target Sequence

<400> SEQUENCE: 25
```

```
tgccaccact gatgaatta                                           19

<210> SEQ ID NO 26
<211> LENGTH: 19
<212> TYPE: DNA
<213> ORGANISM: Artificial
<220> FEATURE:
<223> OTHER INFORMATION: Target Sequence

<400> SEQUENCE: 26
ccatatagag atactcaaa                                           19

<210> SEQ ID NO 27
<211> LENGTH: 19
<212> TYPE: DNA
<213> ORGANISM: Artificial
<220> FEATURE:
<223> OTHER INFORMATION: Target Sequence

<400> SEQUENCE: 27
tctgtcgctt tgagtcaaa                                           19

<210> SEQ ID NO 28
<211> LENGTH: 19
<212> TYPE: DNA
<213> ORGANISM: Artificial
<220> FEATURE:
<223> OTHER INFORMATION: Target Sequence

<400> SEQUENCE: 28
tgcagaatgc tcagagaaa                                           19

<210> SEQ ID NO 29
<211> LENGTH: 19
<212> TYPE: DNA
<213> ORGANISM: Artificial
<220> FEATURE:
<223> OTHER INFORMATION: Target Sequence

<400> SEQUENCE: 29
gcaatcaatg gatgaaagt                                           19

<210> SEQ ID NO 30
<211> LENGTH: 19
<212> TYPE: DNA
<213> ORGANISM: Artificial
<220> FEATURE:
<223> OTHER INFORMATION: Target Sequence

<400> SEQUENCE: 30
gctgaccagt tatgattgt                                           19

<210> SEQ ID NO 31
<211> LENGTH: 19
<212> TYPE: DNA
<213> ORGANISM: Artificial
<220> FEATURE:
<223> OTHER INFORMATION: Target Sequence

<400> SEQUENCE: 31
gagctttgga tcaagttaa                                           19

<210> SEQ ID NO 32
<211> LENGTH: 19
<212> TYPE: DNA
<213> ORGANISM: Artificial
```

```
<220> FEATURE:
<223> OTHER INFORMATION: Target Sequence

<400> SEQUENCE: 32
tggctacaat actgcacaa                                               19

<210> SEQ ID NO 33
<211> LENGTH: 19
<212> TYPE: DNA
<213> ORGANISM: Artificial
<220> FEATURE:
<223> OTHER INFORMATION: Target Sequence

<400> SEQUENCE: 33
ctacaatact gcacaaact                                               19

<210> SEQ ID NO 34
<211> LENGTH: 19
<212> TYPE: DNA
<213> ORGANISM: Artificial
<220> FEATURE:
<223> OTHER INFORMATION: Target Sequence

<400> SEQUENCE: 34
atgatcatag gcagttgaa                                               19

<210> SEQ ID NO 35
<211> LENGTH: 19
<212> TYPE: DNA
<213> ORGANISM: Artificial
<220> FEATURE:
<223> OTHER INFORMATION: Target Sequence

<400> SEQUENCE: 35
ctatgtagtt gtggaagtt                                               19

<210> SEQ ID NO 36
<211> LENGTH: 19
<212> TYPE: DNA
<213> ORGANISM: Artificial
<220> FEATURE:
<223> OTHER INFORMATION: Target Sequence

<400> SEQUENCE: 36
gtggaagttt atgctaata                                               19

<210> SEQ ID NO 37
<211> LENGTH: 19
<212> TYPE: DNA
<213> ORGANISM: Artificial
<220> FEATURE:
<223> OTHER INFORMATION: Target Sequence

<400> SEQUENCE: 37
tgtcgctttg agtcaaaga                                               19

<210> SEQ ID NO 38
<211> LENGTH: 19
<212> TYPE: DNA
<213> ORGANISM: Artificial
<220> FEATURE:
<223> OTHER INFORMATION: Target Sequence

<400> SEQUENCE: 38
gatactagct ttgcagaat                                               19
```

```
<210> SEQ ID NO 39
<211> LENGTH: 19
<212> TYPE: DNA
<213> ORGANISM: Artificial
<220> FEATURE:
<223> OTHER INFORMATION: Target Sequence

<400> SEQUENCE: 39
tttgcagaat gctcagaga                                                19

<210> SEQ ID NO 40
<211> LENGTH: 19
<212> TYPE: DNA
<213> ORGANISM: Artificial
<220> FEATURE:
<223> OTHER INFORMATION: Target Sequence

<400> SEQUENCE: 40
acagctgacc agttatgat                                                19

<210> SEQ ID NO 41
<211> LENGTH: 19
<212> TYPE: DNA
<213> ORGANISM: Artificial
<220> FEATURE:
<223> OTHER INFORMATION: Target Sequence

<400> SEQUENCE: 41
gctgaccagt tatgattgt                                                19

<210> SEQ ID NO 42
<211> LENGTH: 19
<212> TYPE: DNA
<213> ORGANISM: Artificial
<220> FEATURE:
<223> OTHER INFORMATION: Target Sequence

<400> SEQUENCE: 42
cagttatgat tgtgaagtt                                                19

<210> SEQ ID NO 43
<211> LENGTH: 19
<212> TYPE: DNA
<213> ORGANISM: Artificial
<220> FEATURE:
<223> OTHER INFORMATION: Target Sequence

<400> SEQUENCE: 43
gagctttgga tcaagttaa                                                19

<210> SEQ ID NO 44
<211> LENGTH: 19
<212> TYPE: DNA
<213> ORGANISM: Artificial
<220> FEATURE:
<223> OTHER INFORMATION: Target Sequence

<400> SEQUENCE: 44
tggctacaat actgcacaa                                                19

<210> SEQ ID NO 45
<211> LENGTH: 19
<212> TYPE: DNA
<213> ORGANISM: Artificial
<220> FEATURE:
<223> OTHER INFORMATION: Target Sequence
```

<400> SEQUENCE: 45
ctacaatact gcacaaact                                                19

<210> SEQ ID NO 46
<211> LENGTH: 19
<212> TYPE: DNA
<213> ORGANISM: Artificial
<220> FEATURE:
<223> OTHER INFORMATION: Target Sequence

<400> SEQUENCE: 46
atgatcatag gcagttgaa                                                19

<210> SEQ ID NO 47
<211> LENGTH: 19
<212> TYPE: DNA
<213> ORGANISM: Artificial
<220> FEATURE:
<223> OTHER INFORMATION: Target Sequence

<400> SEQUENCE: 47
gtggaagttt atgctaata                                                19

<210> SEQ ID NO 48
<211> LENGTH: 19
<212> TYPE: DNA
<213> ORGANISM: Artificial
<220> FEATURE:
<223> OTHER INFORMATION: Target Sequence

<400> SEQUENCE: 48
ggacacagat ttagacttg                                                19

<210> SEQ ID NO 49
<211> LENGTH: 19
<212> TYPE: DNA
<213> ORGANISM: Artificial
<220> FEATURE:
<223> OTHER INFORMATION: Target Sequence

<400> SEQUENCE: 49
gatggaagca ctagacaaa                                                19

<210> SEQ ID NO 50
<211> LENGTH: 19
<212> TYPE: DNA
<213> ORGANISM: Artificial
<220> FEATURE:
<223> OTHER INFORMATION: Target Sequence

<400> SEQUENCE: 50
cgtgttatct gtcgctttg                                                19

<210> SEQ ID NO 51
<211> LENGTH: 19
<212> TYPE: DNA
<213> ORGANISM: Artificial
<220> FEATURE:
<223> OTHER INFORMATION: Target Sequence

<400> SEQUENCE: 51
tcaccaaagt tgaatcaga                                                19

<210> SEQ ID NO 52

```
<211> LENGTH: 19
<212> TYPE: RNA
<213> ORGANISM: Artificial
<220> FEATURE:
<223> OTHER INFORMATION: Sense Strand

<400> SEQUENCE: 52
caguugccac uuccacaua                                              19

<210> SEQ ID NO 53
<211> LENGTH: 19
<212> TYPE: RNA
<213> ORGANISM: Artificial
<220> FEATURE:
<223> OTHER INFORMATION: Antisense Strand

<400> SEQUENCE: 53
uauguggaag uggcaacug                                              19

<210> SEQ ID NO 54
<211> LENGTH: 25
<212> TYPE: DNA
<213> ORGANISM: Artificial
<220> FEATURE:
<223> OTHER INFORMATION: Sense Strand

<400> SEQUENCE: 54
cagttgccac ttccacataa tgtga                                       25

<210> SEQ ID NO 55
<211> LENGTH: 25
<212> TYPE: RNA
<213> ORGANISM: Artificial
<220> FEATURE:
<223> OTHER INFORMATION: Sense Strand

<400> SEQUENCE: 55
caguugccac uuccacauaa uguga                                       25

<210> SEQ ID NO 56
<211> LENGTH: 27
<212> TYPE: RNA
<213> ORGANISM: Artificial
<220> FEATURE:
<223> OTHER INFORMATION: Antisense Strand

<400> SEQUENCE: 56
ucacauuaug uggaaguggc aacuguu                                     27
```